United States Patent [19]

Polaschegg

[11] Patent Number: 4,711,715
[45] Date of Patent: Dec. 8, 1987

[54] APPARATUS FOR EXTRACORPOREAL TREATMENT OF BLOOD

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 823,887

[22] Filed: Jan. 29, 1986

Related U.S. Application Data

[63] Continuation-in-part of Ser. No. 599,883, Apr. 13, 1984, abandoned.

[30] Foreign Application Priority Data

Apr. 13, 1983 [DE] Fed. Rep. of Germany ....... 3313421

[51] Int. Cl.[4] .............................................. A61M 1/34
[52] U.S. Cl. ...................................... 210/103; 210/137; 210/143; 210/321.71
[58] Field of Search ...................... 210/137, 205, 321.1, 210/321.2, 321.3, 321.4, 321.5, 929, 143, 90, 103, 105

[56] References Cited

U.S. PATENT DOCUMENTS

| | | | |
|---|---|---|---|
| 3,908,653 | 9/1975 | Kettering | 210/90 |
| 4,370,983 | 2/1983 | Lichtenstein | 210/90 |
| 4,469,593 | 9/1984 | Ishihara et al. | 210/90 |

FOREIGN PATENT DOCUMENTS 0042939  1/1982  European Pat. Off. .

Primary Examiner—Ivars Cintins
Attorney, Agent, or Firm—Townsend and Townsend

[57] ABSTRACT

An apparatus for controlling the ultrafiltration rate in machines for the extracorporeal purification of blood in which the difference obtained in the blood circuit by an electromagnetic flow meter is used for controlling the ultrafiltration rate.

The ultrafiltration rate is controlled by controlling the transmembrane pressure across the membrane separating the blood chamber from the dialysis fluid chamber in a dialyzer. In one embodiment, the pressure in the blood circuit is varied to change the transmembrane pressure. In a second embodiment, the pressure in the dialysis solution circuit is varied.

13 Claims, 1 Drawing Figure

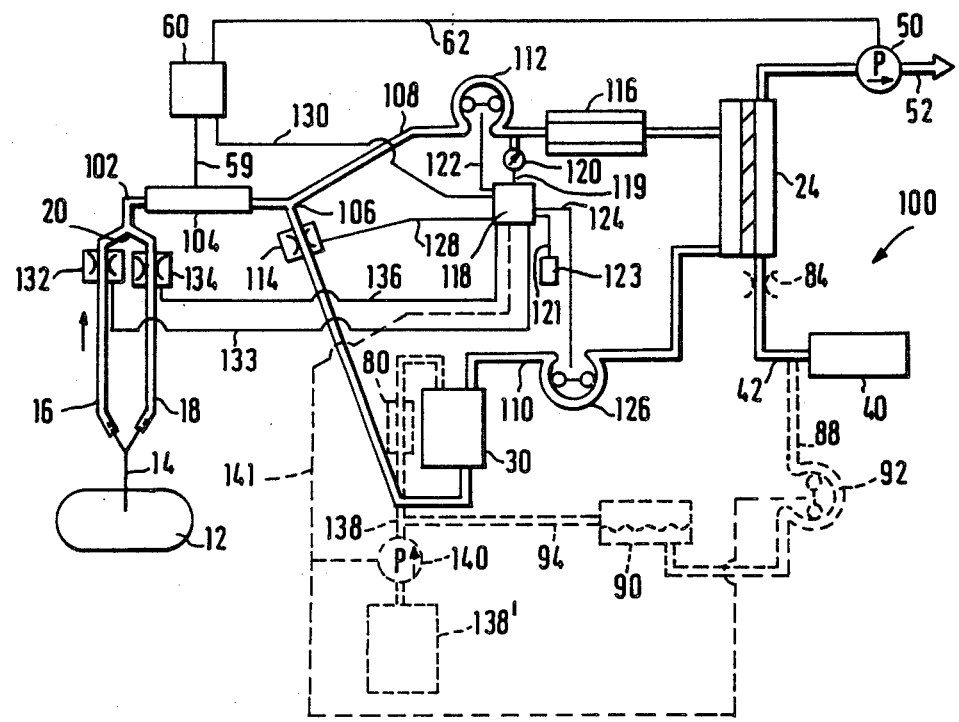

APPARATUS FOR EXTRACORPOREAL TREATMENT OF BLOOD

CROSS-REFERENCE TO RELATED U.S. APPLICATION

This application is a continuation-in-part of my copending U.S. Ser. No. 06/599,883, filed Apr. 13, 1984 and entitled "Apparatus For Extracorporeal Treatment of Blood", now abandoned.

BACKGROUND OF THE INVENTION

The invention relates to a means for controlling the ultrafiltration rate in apparatuses for extracorporeal purification of blood.

It relates in particular to a means for controlling the ultrafiltation rate in hemodialysis apparatuses which comprise a dialyzer having a blood circulation and a dialysis solution circulation, a means for withdrawing ultrafiltrate being provided in the dialysis solution circuit.

In hemodialysis, apart from the metabolism products such as urea, water is also withdrawn from the blood of the patient in the form of ultrafiltrate. It has been found that it is extremely important to control this liquid withdrawal exactly to minimize or avoid the withdrawal problems occurring in the patient. In this connection, in particular the ultrafiltration control is of prime importance. A distinction is to be made between open and closed systems which are realized in single-pass apparatuses.

DE-OS No. 2,644,062 describes a means for automatically controlling a hemodialysis apparatus with open cycle in which in the dialysis solution circuit upstream of the dialyzer a magnetic valve is disposed and downstream of the dialyzer a constant delivery pump is provided.

The magnetic valve is connected to a control unit which controls the magnetic valve in such a manner that a preselected amount of water is continuously withdrawn from the patient during the dialysis. Since however the flow resistance of the dialyzer membrane changes during the dialysis, for example due to clogging and the like, the entire arrangement must be shut down at regular intervals and the flow resistance determined, which firstly is time consuming and secondly above all involves technical problems as regards the apparatus.

This is due on the one hand to the fact that the pump in the dialysis solution circuit carries away the ultrafiltrate whose amount remains small compared with the dialysis solution amount (at the most 1%) and thus cannot be directly determined so that any errors occurring cannot be immediately recognized, and on the other also the fact that the ultrafiltrate itself is not measured until it has already left the blood circulation.

The determination of the ultrafiltrate on the dialysis solution side thus has the disadvantage that for example a slow blood loss to the surroundings, e.g., 10 ml/min, is not detected because the blood loss is not sufficient to effectively change the transmembrane pressure and thus actuate a pressure-sensitive safety device.

The same applies to the withdrawal of blood samples from the blood circuit, which lead to a falsification of the ultrafiltrate determination. In similar manner, an infusion of a replacement fluid into the blood circuit can lead to an unmeasurable change of the ultrafiltrate balance.

DE-PS No. 2,259,787 discloses a hemodialysis apparatus in which liquid is drawn from a closed dialysis solution circulation. However, this apparatus has the disadvantage that the dialysis solution is recirculated so that compared with the single-pass technique the effectiveness of the dialysis is reduced with time due to a decreasing concentration gradient.

A single-pass apparatus having a closed system is known from DE-OS No. 2,838,414 in which balanced dialysis solution which is pumped from and to a balance chamber system is supplied to the dialyzer. Once again, by means of an ultrafiltration pump a predetermined amount of liquid is withdrawn from the closed system and replaced in said system by a corresponding liquid amount which has actually been ultrafiltrated and thus withdrawn from the blood.

A further apparatus known for example from DE-OS No. 3,020,756 determines the ultrafiltration rate from the difference of the incoming and outgoing dialysis solution amounts with the aid of flow meters. The transmembrane pressure can be adjusted so that the ultrafiltration rate corresponds to a predetermined rate.

These known hemodialysis apparatuses have additionally the disadvantage that air bubbles in the dialysis solution can disturb the exact operation of the apparatus because they falsify the ultrafiltration amount. To avoid this, special means are provided, for example air separators.

In addition, these apparatuses involve a high amount of expenditure because the ultrafiltrate amount to be withdrawn of about 2 liters corresponds to a consumption of dialysis solution in the amount of about 120–240 liters, i.e. the ultrafiltration amount is dominated by a relatively large amount of dialysis liquid or solution. Since therefore the amount of ultrafiltrate in the dialysis solution is only about 1–2% the entire apparatus must operate very accurately in the balancing and ultrafiltration in order to avoid endangering the patient.

These known systems thus adjust the ultrafiltration on the side of the dialysis solution without being directly adapted to the conditions of the blood circulation.

DE-OS No. 2,607,022 discloses a hemofiltration apparatus with which the substitution solution is supplied in balanced manner, the pump delivering the substitution solution being controlled with the aid of an ultrasonic flow meter device. Such an ultrasonic flow meter however lacks accuracy because it can determine only a given volume proportion of the liquid flowing in a conduit but not the total liquid amount. Consequently, a change in the flow profile of the liquid or the pulsating flow usual in blood lead to falsifications which make it impossible for such a system to operate accurately. Moreover, such a flow meter cannot be accurately adjusted as is essential.

The ultrafiltration according to this DE-OS has the disadvantage that the ultrafiltration rate can be changed due to clogging of the filter and changes of the blood pressure values in the course of the treatment. Accordingly, with this apparatus a substitution solution is merely supplied without any controlled ultrafiltration being possible, in particular any ultrafiltration independent of a changing blood pressure of changes in the membrane (clogging of the membrane).

In addition, these known apparatuses each comprise an air detector system and systems for detecting blood losses which must be provided independently of the controls of the ultrafiltration and the substitution solution supply. This of course makes the apparatuses expensive, quite apart from the additional sources of possible errors.

It is further to be noted that the known ultrafiltration measuring means or substitution solution control means generally have the disadvantage that they are always designed for a specific method and cannot be combined with each other.

SUMMARY OF THE INVENTION

The problem underlying the invention is therefore to provide a means of the type mentioned at the beginning with which the ultrafiltration can be controlled directly in dependence upon the blood flow parameters.

The solution of this problem is effected in that control of the ultrafiltration rate is through a feedback signal which represents an actual difference between measured blood parameters in the blood circuit. The difference is obtained by an electromagnetic flow meter disposed in the blood circuit.

The apparatus according to the invention first has the advantage that the ultrafiltration rate can be determined directly with the aid of the measured blood parameters. For hitherto the withdrawal of ultrafiltrate was without direct measurement of the conditions in the blood so that a direct control of the ultrafiltration with the aid of the conditions obtaining in the blood was not possible.

According to the invention, the ultlrafiltrate amount directly withdrawn from the blood is measured and compared with a predetermined value. On deviations, the ultrafiltration rate is controlled by controlling the transmembrane pressure. In one embodiment, the transmembrane pressure is regulated by controlling an ultrafiltrate provided in the dialysis solution circuit. In a second embodiment, the pressure in the blood circuit is controlled.

The apparatus according to the invention dispenses with the dialysis solution balancing systems most frequently used at present which permitted an accurate ultrafiltrate measurement and control. Compared with these expensive and technically complicated balancing systems the ultrafiltrate control system according to the invention is considerably simpler, which manifests itself in the costs as well, quite apart from the fact that the ultrafiltrate rate can now be controlled directly and is not dependent on pumps withdrawing constant amounts.

This direct control facility is of particular importance because apparatus faults can be rapidly detected due to the feedback and lead to immediate switching off of the apparatus.

Further details, features and embodiments will be explained with the aid of the following drawing.

BRIEF DESCRIPTION OF THE DRAWING

The single FIGURE shows a schematic arrangement of a hemodialysis apparatus for single-needle treatment.

DESCRIPTION OF PREFERRED EMBODIMENTS

The disclosure of my parent application, Ser. No. 06/599,883, filed Apr. 13, 1984, now abandoned is hereby incorporated by reference.

In the FIGURE an embodiment of a unipuncture or single-needle apparatus 100 is shown with which a single-needle method can be carried out. Accordingly, a Y-shaped needle 14 as usually employed in the single-needle dialysis leads from the patient 12. The one end of the Y-piece is connected to a discharge line 16 whilst the other end of the Y-piece is connected to a supply line 18. The arrows indicated in the drawings show the direction of flow of the blood from and to the patient.

The two lines 16 and 18 unite at 20 and merge into a flexible tube connection 102 which is inserted into a flow meter 104.

As further apparent from the FIGURE in the vicinity of the branch point 20 a first clip 132 is inserted into the outgoing line 16 and is connected via an electrical line 133 to a control unit 118. Furthermore, also in the vicinity of the branch point 20 a second clip 34 is inserted in the supply line 18 and is connected via a further electrical line 136 to the control unit 118.

The two clips 132 and 134 are controlled in push-pull relationship by the control unit 118, i.e. when the clip 132 is open the clip 134 is closed and vice versa.

As the FIGURE also shows, the tube section 102 is restricted substantially only to the region of the flow meter 104, i.e. downstream of the flow meter 104 the tube section branches at 106, and in known manner a tube 108 leading to the dialyzer 24 and a tube 110 leading away from the dialyzer 24 are provided.

The tube section 108 may advantageously comprise a peristaltic blood pump 112 which pumps the blood from the patient through the flow meter 104 and the line 108 to the dialyzer 24 in pumping operation. The tube 110 is closed by a tube clip 114 disposed in the vicinity of the branch point 106. To have available adequate blood volume, for example about 30–35 ml for the dialysis treatment, downstream of the pump 112 there is inserted into the tube section 108 a resilient reservoir 116 in which the blood in pumping operation is buffered and which after stopping of the pump due to the resilient forces acting on the stored blood presses the blood to the dialyzer 24 and into the discharge line 110. The hosepump 112 or 126 acts like a throttle.

As further apparent from the drawing in the discharge line 110 a second peristaltic pump 126 is inserted which is connected via an electrical line 124 to the control unit 118. Furthermore, the control unit 118 is connected via an electrical line 122 to the first blood pump 112. Both pumps are connected in push-pull operation, the clips 114 and 134 and the blood pump 126 being connected synchronously, as are the clip 132 and the blood pump 112.

The control unit 118 is further connected via an electrical line 119 to a pressure sensor 120 which is connected to the supply line 108 downstream of the pump 112 and upstream of the dialyzer.

The control unit 118 is connected via a line 121 to an input means 123 with which preselectable data, for example a definable ultrafiltration rate and/or a definable excess pressure, can be entered into the control unit 118.

The dialyzer 24 further comprises a dialysis solution path, the inlet of the dialyzer being connected to a supply line 42 and the outlet of the dialyzer to a discharge line 52. The supply line 42 is connected to a dialysis solution source 40 whilst the discharge line 52 comprises a delivery pump 50 which pumps the dialysis solution through the dialyzer 24.

According to a preferred embodiment described below said dialysis solution pump 50 may also be used to generate a partial vacuum in the dialysis solution path. For this purpose the pump 50 is connected via a line 62 to an ultrafiltrate controller 60 which is connected via a line 59 to the flow meter 104 and via a line 130 to the control unit 118.

The apparatus 100 illustrated in the FIGURE operates in the following manner:

According to a first preferred embodiment the blood side is controlled via a predetermined pressure whilst the ultrafiltration on the dialysis solution side is set with the reduced pressure generated by the pump 50.

Accordingly, the control unit 118 sets the first pump 112 in operation and at the same time opens the clip 132 until the pressure value indicated at the pressure centre 120 coincides with the entered excess pressure value. Then the clip 132 is closed and the pump 112 stoped whilst the clip 114 is opened and the pump 126 is set in operation. The pump 126 continues to operate until a predetermined lower pressure value is achieved or the pump 126 is operated with a predetermined number of revolutions. Thereafter, the clip 114 is closed again and the pump 126 stopped. Likewise, the clip 134, which was open during this half cycle, is closed again.

The first half cycle then starts again.

On the dialysis solution side the pump 150 generates a predetermined partial vacuum or reduced pressure which in turn effects a predetermined ultrafiltration rate through the dialyzer. This ultrafiltation rate can be measured with the aid of a single flow meter 104 which is connected to the flow controller 60.

Since by the ultrafiltration water is withdrawn from the blood, the flow rate of the blood changes. During the first half cycle, unpurified blood flows through the flow meter 104; during the second half cycle, purified blood flows through the flow meter 104. This results in different measurement parameters which are transmitted by the flow meter to the ultrafiltrate controller 60. On the basis of the difference in parameters, the ultrafiltration rate may be determined.

The desired ultrafiltration rate can be entered with the input device 123 into the control unit 118. As a result, via the line 130 the measured actual value can be compared with the entered desired value and thus a control of the pump effected. By increasing or decreasing the number of revolutions of the pump the reduced pressure in the dialysis solution path and thus the ultrafiltration can be controlled.

According to a second embodiment, however, on the blood side as well an excess pressure can be exerted on the blood volume included between the pump 112 and the pump 126. For this purpose the peristaltic blood pump 126 blocks the line 110. With the aid of the blood pump 112 blood is pumped into the resilient reservoir 116 and into the blood chamber of the dialyzer, the pressure sensor 120 passing the pressure value arising onto the control unit 118. At a predetermined excess pressure the pump 112, as explained below, is then switched off and the pump 126 switched on so that the excess pressure generated is diminished.

The excess pressure value at which the changeover occurred with the aid of the control unit 118 is associated with a predetermined ultrafiltration rate. This correlation is made by the ultrafiltrate controller 60 which receives the corresponding signal from the control unit 118 via the line 130.

Previously, a predetermined ultrafiltration rate or a program with which the time sequence of the ultrafiltration rate can be controlled has been entered via the input device 123 into the control unit 118.

As explained above, the ultrafiltration rate is determined with the aid of the flow meter 104 in the time intervals indicated, the ultrafiltrate controller 60 storing the particular actual value of the ultrafiltration. This actual value is correlated with a predetermined excess pressure value at which the switchover of the operating elements of the blood circuit takes place. This correlation is stored in the control unit 118, a desired value/actual value comparison being made with the result that when a deviation of the values occurs the excess pressure value is regulated. If for example the ultrafiltration rate is too high, following the ultrafiltration rate signal the changeover signal occurring at the pressure sensor is reduced, i.e. the control unit 118 switches the pump 112 off at a lower excess pressure and switches the pump 126 on simultaneously. If however the ultrafiltration rate is too low the control unit 118 increases the excess pressure, i.e. the pump 112 pumps for a longer time than in the previous cycle, that is until the desired excess pressure is reached.

In the above case of course the pump 50 does not serve to generate a reduced pressure in the dialysis solution path but instead solely to pump the dialysis solution through the dialyzer 24.

With the embodiment shown in the FIGURE hemofiltration and hemodiafiltration may also be carried out, a drip chamber 30 then being connected into the discharge line 110, said chamber being connected via a line section 138 shown in dashed line to a substitution fluid reservoir 138'. A substitution pump 140 is connected into the line 138.

With this hemodiafiltration apparatus a relatively large ultrafiltrate amount is replaced by almost the same amount of a substitution fluid. Accordingly, the pump 50 during the entire treatment pumps off $10 \propto 20$ liters filtrate which minus the ultrafiltrate amount actually to be removed must be replaced by a substitution fluid which is added directly to the blood circulation downstream of the dialyzer 24.

Conveniently, this substitution fluid is introduced into the drip chamber 30 from the reservoir 138' via the tubing 138 with the aid of the pump 140. Advantageously, the pump 140 can be regulated so that the rate with which the substitution fluid is supplied to the venous drip chamber 30 can be adjusted. For this purpose the pump 140 is connected via an electrical line 141 to the control unit 118 which with the aid of ultrafiltrate controller 60 coordinates the pumping rates of the two pumps 50 and 140.

Advantageously, one of the two pumps may be set to a predetermined pumping rate whilst the other pump is regulated in its pumping rate with the aid of the flow meter 104 and ultrafiltrate controller 60 to obtain the desired amount of ultrafiltrate.

The control can take place according to one of the two above methods, i.e. either on the reduced pressure side with the aid of the pump 50 or on the excess pressure side with the aid of the pump 112.

Furthermore, a heating means 80 may advantageously be connected into the tubing 138. The heating means 80 heats the substitution fluid, taken sterilely from the reservoir 138', to the body temperature.

As already mentioned above, one of the two pumps is set to a predetermined pumping rate whilst the other pump is regulated. Advantageously, the pump 140 is set to the desired exchange rate. The ultrafiltrate controller 60 then sets the desired liquid withdrawal or ultrafiltration rate at the pump 50 and 112 respectively.

This hemodiafiltration apparatus can of course also be used as pure hemofiltration apparatus or plasma filtration apparatus. For this purpose, it is only necessary to clamp off the tubing section 42 or seal the dialysis solution inlet of the dialyzer 24.

A further hemodiafiltration apparatus in a further improved embodiment is shown in the FIGURE, the parts represented also being drawn in dashed line.

In this embodiment the substitution fluid used according to the embodiment described above is a sterilely filtered dialysis solution. This has the advantage that the usually expensive substitution fluid which because of its sterile and pyrogen-free properties had to be prepared by the manufacturer, is replaced by a usual dialysis solution which is filtered sterile and pyrogen-free at the bedside.

Accordingly, the dialysis solution is again provided in the dialysis solution reservoir 40 and can be withdrawn therefrom via the line 42. Connected into said line is a throttle 84 as flow resistance which can also be used to adjust the pressure between the pump 50 and the throttle 84. Moreover, the closure of the throttle 84 changes the apparatus from a hemodiafiltration apparatus to a hemofiltration apparatus.

Upstream of the throttle 84 from the tubing 42 a tubing 88 branches off which is connected to the input of a filter 90. Also connected into said tubing 88 is a pump 92 which pumps dialysis solution from the reservoir 40 to the filter 90 in which the purification of the dialysis solution takes place which is thus sterile and pyrogen-free downstream of the filter 90. This purified dialysis or substitution solution leaves the filter 90 via a tubing 94 which is again connected to the drip chamber 30. In the FIGURE this line 94 is connected for clarity to the line 138 but this need not necessariy be the case. Advantageously, the heating means 80 is again however provided in the line 94.

The pump 92 is again connected via the line 141 to the control unit 118, i.e. is operated corresponding to the pump 140 so that the latter can be referred to.

Moreover, the mode of operation of this apparatus also corresponds to the mode of operation described above of the first hemodiafiltration apparatus so that reference can be made thereto.

Filter 90 may comprise a conventional hemodialysis filter in which only two connections are employed so that the other connections are sealed.

Of course, this embodiment can also be employed as hemofiltration and plasma filtration apparatus. In this case the throttle 84 shuts off the tubing 42 or alternatively the dialysis solution inlet of the dialyzer 24 is closed.

As flow meters, fundamentaly all known flow meters are possible. Since however a blood flow is to be measured flow meters operating practically contactless are to be preferred, i.e. ultrasonic flow meters, electromagnetic flow meters and thermal flow meters. Particularly preferred are electromagnetic flow meters.

Such a flow meter should operate so accurately that during the treatment time substantially no changes of its measurement behavior occur. Only then is it ensured that the difference formation can be considered exact.

According to a further preferred embodiment the line section 102 consists of a substantially rigid plastic material, for example hard PVC or polycarbonate, and thus does not have any yielding properties, i.e. compliance. Such a plastic tube can either be inserted into a flow meter or it is equipped with elements, for example electrodes, which are implemented in the tube and form the flow meter.

I claim:

1. In a hemodialysis apparatus comprising a first chamber, a second chamber, a dialysis solution circuit, a blood circuit, means for preparing a fresh dialysis solution, and means for withdrawing ultrafiltrate from said dialysis circuit, said first chamber being separated by means of a membrane from said second chamber, said first chamber being connected into said dialysis solution circuit, and said second chamber being connected into said blood circuit, said blood circuit including a first blood side upstream of said second chamber and a second blood side downstream of said second chamber, the improvement comprising:

a single sensor coupled between a single connection with a patient and a branch of said blood circuit into said first and second blood sides, said sensor alternately sensing inflowing blood quantities and outflowing blood quantities;

an ultrafiltrate controller coupled to said sensor for receiving signals from said sensor and being operative during a first time interval to recognize a first output signal from said sensor representing outflowing blood quantities and being operative during a second time interval to recognize a second output signal from said sensor representing inflowing blood quantities and being operative after said first and second time intervals to compare said first output signal with said second output signal to determine the actual ultrafiltration rate;

a control unit connected to said ultrafiltrate controller, said control unit having input means for inputting a predetermined ultrafiltration rate; and a dialysis solution pump coupled in said dialysis circuit downstream of said first chamber and operatively coupled to said ultrafiltrate controller for changing the pressure in said dialysis solution circuit, thereby changing the transmembrane pressure to cause the actual ultrafiltration rate to approach said predetermined ultrafiltration rate.

2. The apparatus according to claim 1, the improvement further comprising:

a first blood pump connected in said first blood side and operatively coupled to said control unit;

a second blood pump connected in said second blood side and operatively coupled to said control unit; and a pressure sensor connected to said first blood side downstream of said first blood pump and coupled to said control unit;

said control unit being operative during said first time interval to activate said first blood pump and to deactivate said second blood pump and said control unit being operative during said second time interval to activate said third pump and to deactivate said second pump, and said control unit being operative to effectuate a switchover from said first time interval to said second time interval when said pressure sensor indicates to said control unit a pressure value which matches a predetermined excess pressure value.

3. In the apparatus of claim 2, the improvement further comprising:

a supply line connected to said single connection with said patient;

a discharge line connected to said single connection with said patient;

a tube section connecting said discharge line and said supply line to said sensor;

a supply line clip in said supply line operatively coupled to said control unit;

a discharge line clip in said discharge line operatively coupled to said control unit; and a tube clip in said second blood side downstream of said second blood pump and operatively coupled to said control unit;

said control unit being operative during said first time interval to open said discharge line clip, and to close said supply line clip and to close said tube clip, said control unit being operative during said second time interval to close said discharge clip and to open said supply line clip and to open said tube clip.

4. The apparatus according to claim 1 wherein said sensor includes a flow meter.

5. The apparatus according to claim 1 wherein said sensor includes an electromagnetic flow meter.

6. In the apparatus of claim 1, the improvement further including a drip chamber, a substitution fluid reservoir and a substitution fluid pump, said drip chamber being disposed in said second blood side and being operative to receive fluid from said second chamber, said substitution fluid reservoir being coupled to said drip chamber for providing substitution fluid into said drip chamber via said substitution fluid pump, said control unit being operatively coupled to said substitution fluid pump for coordinating the pumping rates of said substitution fluid pump and said dialysis solution pump.

7. In the apparatus according to claim 1, the improvement further comprising a drip chamber, a dialysis solution reservoir, and a filter, said drip chamber being coupled in said second blood side and said dialysis solution reservoir being connected to said drip chamber via said filter.

8. In a hemodialysis apparatus comprising a first chamber, a second chamber, a dialysis solution circuit, a blood circuit, means for preparing a fresh dialysis, solution, and means for withdrawing ultrafiltrate from said dialysis circuit, said first chamber being separated by means of a membrane from said second chamber, said first chamber being connected into said dialysis solution circuit, and said second chamber being connected into said blood circuit, said blood circuit including a first blood side upstream of said second chamber and a second blood side downstream of said second chamber, the improvement comprising:

a single sensor coupled between a single connection with a patient and a branch of said blood circuit into said first and second blood sides, for alternately sensing inflowing blood quantities and outflowing blood quantities;

an ultrafiltrate controller coupled to said sensor for receiving signals from said sensor and being operative during a first time interval to recognize a first output signal representing outflowing blood quantities and being operative during a second time interval to recognize a second output signal representing inflowing blood quantities and being operative to compare said first output signal with said second output signal to determine the actual ultrafiltration rate;

a control unit connected to said ultrafiltrate controller, said control unit having input means for inputting a desired ultrafiltration rate;

a first pump connected in said first blood side and operatively coupled to said control unit;

a second pump connected in said second blood side and operatively coupled to said control unit; and a pressure sensor connected in said first blood side downstream of said first pump and coupled to said control unit;

said control unit being operative during said first time interval to activate said first pump and to deactivate said second pump and being operative during said second time interval to deactivate said first pump and to activate said second pump, said control unit being operative to effectuate a switchover from said first time interval to said second time interval when said pressure sensor indicates to said control unit a pressure value which matches an excess pressure value, said control unit being further operative to determine said excess pressure value by comparing said actual ultrafiltration rate and said desired ultrafiltration rate.

9. In the apparatus of claim 8, the improvement further comprising:

a supply line connected to said single connection with said patient;

a discharge line connected to said single connection with said patient;

a tube section connecting said discharge line and said supply line to said sensor;

a supply line clip in said supply line operatively coupled to said control unit;

a discharge line clip in said discharge line operatively coupled to said control unit; and a tube clip in said second blood side downstream of said second pump and operatively coupled to said control unit;

said control unit being operative during said first time interval to open said discharge clip, and to close said supply line clip and to close said tube clip, said control unit being operative during said second time interval to close said discharge clip and to open said supply line clip and to open said tube clip.

10. The apparatus according to claim 8 wherein said sensor includes a flow meter.

11. The apparatus according to claim 8 wherein said sensor includes an electromagnetic flow meter.

12. In the apparatus of claim 8, the improvement further including a drip chamber, a substitution fluid reservoir and a substitution fluid pump, said drip chamber being disposed in said second blood side and being operative to receive fluid from said second chamber, said substitution fluid reservoir being coupled to said drip chamber for providing substitution fluid into said drip chamber via said substitution fluid pump, said control unit being operatively coupled to said substitution fluid pump for controlling the pumping rate of said substitution fluid pump.

13. In the apparatus according to claim 8, the improvement further comprising a drip chamber, a dialysis solution reservoir, and a filter, said drip chamber being coupled in said second blood side and said dialysis solution being connected to said drip chamber via said filter.

* * * * *